United States Patent
AlHazmi

(10) Patent No.: US 9,914,686 B1
(45) Date of Patent: Mar. 13, 2018

(54) METHOD OF PRODUCING FATTY ALCOHOLS

(71) Applicant: SABIC GLOBAL TECHNOLOGIES B.V., Bergen op Zoom (NL)

(72) Inventor: Naeem Rabeeh AlHazmi, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/554,444

(22) PCT Filed: Apr. 22, 2016

(86) PCT No.: PCT/IB2016/052313
§ 371 (c)(1),
(2) Date: Aug. 30, 2017

(87) PCT Pub. No.: WO2016/170514
PCT Pub. Date: Oct. 27, 2016

Related U.S. Application Data

(60) Provisional application No. 62/152,527, filed on Apr. 24, 2015.

(51) Int. Cl.
*C07C 29/80* (2006.01)
*C07C 31/125* (2006.01)
(Continued)

(52) U.S. Cl.
CPC .............. *C07C 29/80* (2013.01); *B01D 3/14* (2013.01); *C07C 31/125* (2013.01); *C11B 3/12* (2013.01); *C11B 11/00* (2013.01)

(58) Field of Classification Search
CPC ......... C07C 29/80; C07C 31/125; B01D 3/14; C11B 3/12; C11B 11/00
See application file for complete search history.

(56) References Cited

U.S. PATENT DOCUMENTS 4,645,570 A 2/1987 Sridhar et al.
8,569,550 B2 10/2013 McKinley et al.

FOREIGN PATENT DOCUMENTS

CN 102838449 A 12/2012
DE 102007038919 A1 2/2009
(Continued)

OTHER PUBLICATIONS

Chinese Patent No. 102838449; Date of Publication: Dec. 26, 2012; Abstract Only, 1 page.
(Continued)

*Primary Examiner* — Yate' K Cutliff
(74) *Attorney, Agent, or Firm* — Cantor Colburn LLP

(57) ABSTRACT

A method of producing fatty alcohols comprises: introducing a fatty alcohol feedstock stream to a distillation column; forming a light outlet stream and a heavy outlet stream; condensing at least a portion of the light outlet stream to form a reflux stream; returning the reflux stream to a reflux inlet of the distillation column at a reflux ratio of greater than or equal to 2; and recovering a fatty alcohol product stream from an outlet of the distillation column, wherein the fatty alcohol product stream comprises a first mass percentage of the first fatty alcohol species (M), and a second mass percentage of the second fatty alcohol species (M2), and wherein a fatty alcohol mass ratio ($M_1/M_2$) of the fatty alcohol product stream is the first mass percentage divided by the second mass percentage, and wherein the fatty alcohol mass ratio is greater than or equal to 2.0.

20 Claims, 1 Drawing Sheet

(51) Int. Cl.
*B01D 3/14* (2006.01)
*C11B 11/00* (2006.01)
*C11B 3/12* (2006.01)

(56) References Cited

FOREIGN PATENT DOCUMENTS

| EP | 1550649 A1 | 7/2005 |
| WO | 2010116164 A1 | 10/2010 |
| WO | 2014128058 A2 | 8/2014 |

OTHER PUBLICATIONS

International Search Report for International Application No. PCT/IB2016/052313; International Filing dated Apr. 22, 2016; dated Jul. 27, 2016; 6 Pages.

Johannisbauer W. et al. "Die Destillative Aufarbeitung Oleochemischer Stoffe. The Distillation of Oleochemical Products," FETT—LIPID Science Technology, Wiley-VCH Verlag, Weinheim, vol. 98, No. 12, Dec. 1, 1996, ISSN: 0931-5985; pp. 402-408.

Written Opinion of the International Searching Authority for International Application No. PCT/IB2016/052313; International Filing dated: Apr. 22, 2016; dated Jul. 27, 2016; 6 Pages.

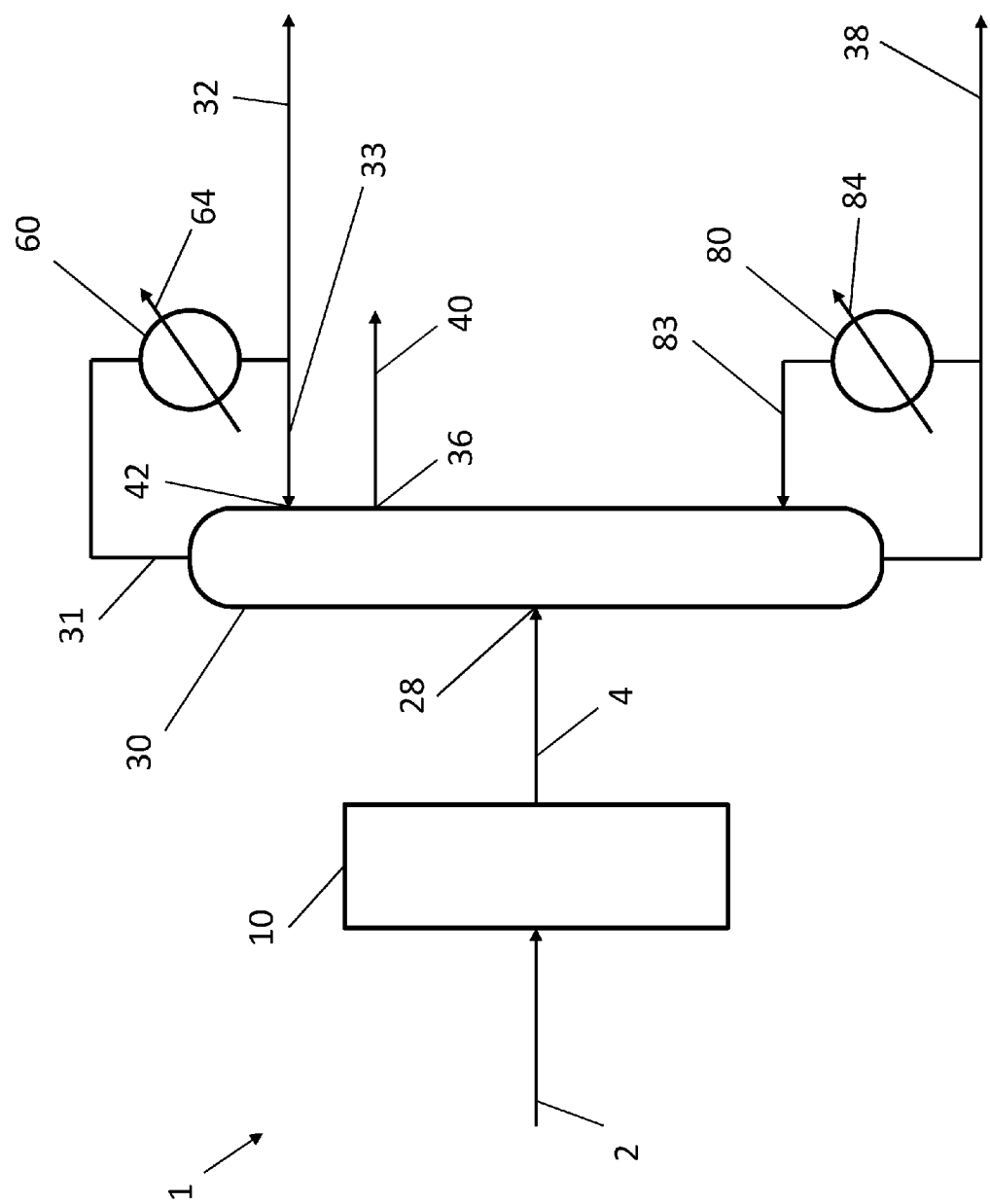

METHOD OF PRODUCING FATTY ALCOHOLS

CROSS REFERENCE TO RELATED APPLICATIONS

This application is a 371 of International Application No. PCT/IB2016/052313, filed Apr. 22, 2016 and U.S. Application Ser. No. 62/152,527, filed Apr. 24, 2015 which are incorporated herein by reference in their entirety.

BACKGROUND

Fatty alcohols can include alkanes or alkenes having an alcohol (or hydroxyl) functional group. The carbon chain length of fatty alcohols can vary from 4 carbons to about 34 carbons. The alcohol group can be attached to the carbon chain, for example, at a terminal carbon.

Physically these alcohols can be oily liquids or can be waxy solids depending on the length of their carbon chain and can be used in the production of detergents, surfactants, cosmetics, foods, and as industrial solvents. Fatty alcohols can exhibit $C_{12}$ amphipathic nature, having both hydrophilic and lipophilic ends and can behave as nonionic surfactants. They can find use as emulsifiers, emollients, and thickeners, for example, in cosmetics and food industry.

BRIEF DESCRIPTION

Disclosed herein are method s of producing fatty alcohols, and the alcohols produced therefrom.

A method of producing fatty alcohols comprises: introducing a fatty alcohol feedstock stream to a distillation column; forming a light outlet stream and a heavy outlet stream; condensing at least a portion of the light outlet stream to form a reflux stream; returning the reflux stream to a reflux inlet of the distillation column at a reflux ratio of greater than or equal to 2; and recovering a fatty alcohol product stream from an outlet of the distillation column, wherein the fatty alcohol product stream comprises a first mass percentage of the first fatty alcohol species ($M_1$), and a second mass percentage of the second fatty alcohol species ($M_2$), and wherein a fatty alcohol mass ratio ($M_1/M_2$) of the fatty alcohol product stream is the first mass percentage divided by the second mass percentage, and wherein the fatty alcohol mass ratio is greater than or equal to 2.0.

The above described and other features are exemplified by the following FIGURES and detailed description.

BRIEF DESCRIPTION OF THE DRAWINGS

Refer now to the FIGURES, which are exemplary embodiments, and wherein the like elements are numbered alike.

FIG. 1 is an illustration of an embodiment of a process for producing a fatty alcohol product stream.

DETAILED DESCRIPTION

Fatty alcohols may be derived either from natural sources or they may be synthesized, e.g., from a fossil fuel feedstock such as petroleum. Because fatty alcohols (e.g., particularly fatty alcohols comprising 10-20 carbon atoms) are often used in the production of synthetic detergents, they are sometimes referred to as detergent alcohols or detergent range alcohols.

Detergent range alcohols can be produced by hydrogenation of an alkyl ester, such as methyl ester or ethyl ester, of the corresponding carboxylic acids (e.g., hydrogenation of methyl laurate (methyl dodecanoate) to form lauryl alcohol (dodecanol)). The alkyl ester can be produced by various methods. For example, an alkyl ester can be produced by transesterification of a triglyceride, by esterification of a carboxylic acid (such as those obtained by hydrolysis of a triglyceride), or can be synthesized from fossil fuels such as petroleum or natural gas. Examples of natural triglycerides which can be used as raw materials include natural oils, such as coconut oil, rape seed oil and palm oils, animal fats such as lard, tallow and fish oil, or a combination including at least one of the foregoing. As these starting materials can contain mixtures of chemicals having a variety of hydrocarbon chain lengths the alcohol products obtained from their hydrogenation can include mixtures of alcohols of differing molecular formulas. For example, up to three different esters (e.g., having different carbon chain lengths) can be derived from a single triglyceride molecule. In another example, esters synthesized from fossil fuels can have a range of carbon chain lengths resulting from the mixture of hydrocarbon species present in the fossil fuel.

However, it can be desirable for manufacturers to produce a fatty alcohol product stream having a selected distribution of carbon chain lengths (or grade of fatty alcohols). Providing such a product stream can simplify subsequent processes by reducing equipment size (e.g., reducing capital cost), eliminating waste streams, eliminating by-product streams, increasing production efficiency, or a combination including at least one of the foregoing. Thus, a product stream can comprise fatty alcohols having chain lengths differing by one to three carbon atoms. Examples of these alcohol product compositions can include any mixture of fatty alcohol species, such as mixtures containing 6-8 carbon atoms ($C_6$-$C_8$), 8-10 carbon atoms ($C_8$-$C_{10}$), 12-14 carbon atoms ($C_{12}$-$C_{14}$), or 16-18 carbon atoms ($C_{16}$-$C_{18}$). The alcohol product composition can include mixtures containing 12-14 carbon atoms ($C_{12}$-$C_{14}$). The alcohol product composition can include mixtures containing 8-10 carbon atoms ($C_8$-$C_{10}$). The alcohol product composition can include mixtures containing 6-8 carbon atoms ($C_6$-$C_8$) and/or 16-18 carbon atoms ($C_{16}$-$C_{18}$).

The composition of the fatty alcohol product stream can be further manipulated for a selected end use by adjusting the distribution of fatty alcohols in the stream. For example, the fatty alcohol product stream can comprise a specific ratio of a first fatty alcohol having a first carbon chain length to a second fatty alcohol having a second carbon chain length. Adjusting this ratio can be desirable to meet the market demand for a chosen end use of a fatty alcohol mixture. Thus, a producer may desire to provide a fatty alcohol product stream composition containing a selected mass ratio ($M_1$:$M_2$) of the mass of a first fatty alcohol ($M_1$) to the mass of a second fatty alcohol ($M_2$). The first fatty alcohol can have a greater number of carbon atoms than the second fatty alcohol. For example, a first fatty alcohol can comprise 12 carbon atoms ($C_{12}$, also referred to as lauryl alcohol or dodecanol) and a second fatty alcohol can comprise 14 carbon atoms ($C_{14}$, also referred to as myristyl alcohol or tetradecanol). A producer can target production of a fatty alcohol product stream comprising a ratio of 3:1 ($M_1$:$M_2$).

Yet, the vapor pressure of a first fatty alcohol species having a first carbon chain length can be close to that of a second fatty alcohol species having a second carbon chain length at a selected temperature. So it can be difficult to adjust the mass ratio of the fatty alcohols in the fatty alcohol product stream through separation processes reliant on differences in volatility, such as simple distillation.

Fractional distillation can be employed to provide more adjustable parameters in the separation process (e.g., location of fatty alcohol product stream removal from the distillation column), and can be used to help adjust the ratio of fatty alcohols in a fatty alcohol product stream. By selecting the location (e.g., outlet height, outlet tray number, or the like) where the fatty alcohol product stream is removed from the fractional distillation column a desired product grade can be achieved (e.g., a mixture comprising a pre-selected set of species, such as $C_{12}$ and $C_{14}$ fatty alcohols), yet the mass ratio of the fatty alcohols in that grade are limited by thermodynamics governing the distillation at the chosen removal location. So while it is possible to limit the product mixture to a specific grade by choosing a recovery location from the column, the ratio of the species in the grade can be fixed at that point. For example, the mass ratio of $C_{12}$ fatty alcohol to $C_{14}$ fatty alcohol can be fixed for a given removal location in a fatty alcohol product stream comprising $C_{12}$ and $C_{14}$ fatty alcohols.

A method of adjusting the mass ratio of the first fatty alcohol species to the second fatty alcohol species in the fatty alcohol product stream can include adjusting a reflux ratio of the distillation column. A reflux section of the distillation column can include a condenser which cools and condenses a vapor phase product recovered from the top of the distillation column to form a liquid stream which can be returned to an inlet of the distillation column. The reflux ratio (R) of the distillation column is defined as the mass flow rate of liquid returned to the column ($L_c$) divided by the mass flow rate of an overhead product (D), where the total mass flow rate from the top of the column equals $L_c+D$.

Increasing the reflux ratio can increase the concentration of high volatility species (e.g., light species, such as the first fatty alcohol species), and can reduce the concentration of low volatility species (e.g., heavy species, such as the second fatty alcohol species), in the overhead product. This effect can cascade down the column, and can result in an increased concentration of light species in the overhead streams (e.g., tops or light ends) and a reduced concentration of heavy species in the overhead streams. Combining this effect with using a side recovery stream, such as an outlet located at a location below the overhead product outlet and above the feed inlet location, can result in a fatty alcohol product stream comprising less light species and more heavy species. Thus, by controlling the reflux ratio and removing a fatty alcohol product stream from a side recovery outlet it is possible to control the mass ratio of the first fatty alcohol to the second fatty alcohol ($M_1:M_2$).

Surprisingly, it has been found that the combination of increasing the reflux ratio and choosing a side recovery location is able to achieve a mass ratio of a first fatty alcohol to the second fatty alcohol ($M_1:M_2$) of 3:4 to 4:1, or, 1:1 to 3:1, or 2:1 to 3:1. For example, the mass percentage of the fatty alcohol product stream can include 75 mass % of a first fatty alcohol and 25 mass % of a second fatty alcohol, or 70 mass % of the first fatty alcohol and 30 mass % of the second fatty alcohol. Moreover, a fatty alcohol mass ratio ($M_1/M_2$) of the fatty alcohol product stream can be greater than or equal to 2.0, for example, 2.0 to 3.0, or, 2.15 to 2.45, or 2.30 to 2.36, where the fatty alcohol mass ratio is defined as the mass percentage of the first fatty alcohol species divided by the mass percentage of the second fatty alcohol species in the fatty alcohol product stream. The Applicants found that these results were not achievable merely by adjusting other operating parameters of an existing fractional distillation column, such as pressure, temperature, feed rate, recovery rate, condenser duty, reboiler duty, fatty alcohol product stream removal location, or a combination including at least one of the foregoing operating parameters.

FIG. 1 is an illustration of a process 1 for producing a fatty alcohol product stream 40. The process 1 includes a feedstock production section 10 and a distillation column 30. The feedstock production section 10 can process a feedstock stream 2 comprising a fossil fuel into a fatty alcohol feedstock stream 4 comprising a first fatty alcohol species and a second fatty alcohol species. The first fatty alcohol species can comprise fewer carbon atoms than the second fatty alcohol species. The first fatty alcohol species can comprise 6 carbon atoms and the second fatty alcohol species can comprise 8 carbon atoms. The first fatty alcohol species can comprise 8 carbon atoms and the second fatty alcohol species can comprise 10 carbon atoms. The first fatty alcohol species can comprise 12 carbon atoms and the second fatty alcohol species can comprise 14 carbon atoms. The first fatty alcohol species can comprise 16 carbon atoms and the second fatty alcohol species can comprise 18 carbon atoms. The feedstock production section 10 can process the feedstock stream into the fatty alcohol feedstock stream 4 by any suitable chemical reaction process, for example an esterification and dehydration process can be employed. The fatty alcohol feedstock stream 4 can be introduced to the distillation column 30 at a feed inlet 28. The distillation column 30 can separate the fatty alcohol feedstock stream 4 into a light outlet stream 32, a heavy outlet stream 38, and the fatty alcohol product stream 40. The light outlet stream 32 can contain a higher mass percentage of light species (e.g., species having a lower boiling point temperature, lower volatility, lower vapor pressure at a given temperature, or a combination including at least one of the foregoing) in comparison to the heavy outlet stream 38. The heavy outlet stream 38 can contain a higher mass percentage of heavy species (e.g., species having a higher boiling point temperature at a given pressure, higher volatility, higher vapor pressure at a given temperature, or a combination including at least one of the foregoing) in comparison to the light outlet stream 32.

The distillation column 30 can be operated with a condenser 60, a reboiler 80, or a combination comprising at least one of the foregoing. The condenser 60 can include any suitable heat exchanger. The condenser 60 can utilize a cooling fluid stream 64 to condense at least a portion of the overhead stream 31 to form a reflux stream 33 comprising a liquid, and the light outlet stream 32 comprising a gas. The cooling fluid stream 64 can comprise any suitable heat exchange fluid, e.g., air, water, glycol, oil, or the like. The reflux stream 33 can be returned to a reflux inlet 42 of the distillation column 30 at a reflux mass flow rate. The operation of the distillation column 30 can comprise returning the reflux stream 33 to the distillation column 30 at a reflux ratio (R) of greater than or equal to 2, for example, greater than or equal to 25 or, greater than or equal to 45, or a reflux ratio of 2 to 200, or, 2 to 100, or 10 to 75, or 25 to 50. Where the reflux ratio (R) is defined as the mass flow rate of the reflux stream 33 divided by the mass flow rate of the light outlet stream 32. The fatty alcohol product stream 40 can comprise a first mass percentage ($M_1$) of a first fatty alcohol species and a second mass percentage ($M_2$) of a second fatty alcohol species. The fatty alcohol product stream 40 can comprise a fatty alcohol mass ratio ($M_1/M_2$) of greater than or equal to 2.0, for example, 2.0 to 3.0, or, 2.15 to 2.45, or 2.30 to 2.36. The distillation column 30 can be operated with a reflux ratio of greater than or equal to 10 and provide a fatty alcohol mass ratio of the fatty alcohol product stream 40 of 2.30 to 2.36. The reflux inlet 42 of the distillation column 30 can be located above the feed inlet 28 and below the top of the column. The fatty alcohol product stream 40 can be recovered from a side outlet 36 of the distillation column 30. The side outlet 36 can be located above the feed inlet 28 and below the reflux inlet 42. The side outlet 36 can be located in an enriching section (also referred to as a rectification section) of the distillation column.

The distillation column 30 can include any suitable internals. For example, internals can include structured packing (e.g., corrugated metal sheets, meshs, guazes, foams and the like), random packing (e.g., Berl Saddles, Raschig rings, Pall Rings, Lessing Rings, and the like), plates, trays, weirs, sieves, valve, downcomers, or a combination comprising at least one of the foregoing. The distillation column internals can be chosen to provide a desired liquid/vapor interfacial area, residence time, pressure drop, liquid distribution, liquid holdup, or a combination of the foregoing, while accounting for fouling, corrosion, degradation, operating efficiency, flooding and the like.

The reboiler 80 can be various reboilers, such as a kettle reboiler, fired reboiler, thermosyphon reboiler, forced circulation reboiler, heat exchanger or the like. The reboiler 80 can utilize a heat transfer fluid stream 84 to transfer heat into the distillation column 30. The heat transfer fluid can include any suitable fluid, such as steam, oil, engineered heat transfer fluids, or the like. The reboiler 80 can heat the fluids in the distillation column 30 sufficiently to vaporize a portion of the heavy outlet stream. The heated fluid (e.g., liquid, vapor, or two-phase liquid and vapor) can be returned to the distillation column 30 via the reboiler return stream 83.

It is noted that FIG. 1 depicts the condenser 60 and reboiler 80 as separate units removed from the column proper. However, this is simply for ease of description and the condenser 60 and/or reboiler 80 can be integral to the column. Additionally, the positioning of the various streams as described herein as being, e.g., in the "top", "middle", "bottom", or "side" of a particular vessel is relative because the actual position at which material is to be introduced or recovered is dependent on the conditions being maintained in the particular vessel. For example, a stream entering the "bottom" of the distillation column 30 can actually enter several stages above (or some distance above) the sump including the reboiler 80, and a line/stream exiting the "top" of the column can actually exit several stages below (or some distance below) the top stage including the condenser 60. Thus, such terms herein are included for ease of reference to describe a general orientation regarding various vessels and streams and such terms are not meant to be limiting to one exact location. Also, although for illustrative purposes, FIG. 1 and the accompanying description depicts singular vessels, such as feedstock production section 10 and distillation column 30, it is understood that multiple vessels in series or parallel can be used where suitable.

Set forth below are some embodiments of the methods disclosed herein.

Embodiment 1

A method of producing fatty alcohols comprising: introducing a fatty alcohol feedstock stream comprising a first fatty alcohol species and a second fatty alcohol species to a distillation column; wherein the first fatty alcohol species comprises fewer carbon atoms than the second fatty alcohol species; separating the fatty alcohol feedstock stream by a distillation process to form a light outlet stream and a heavy outlet stream; condensing at least a portion of the light outlet stream to form a reflux stream comprising a reflux mass flow rate and a light product stream comprising a light product mass flow rate; returning the reflux stream to a reflux inlet of the distillation column at a reflux ratio defined as the reflux mass flow rate divided by the light product mass flow rate, wherein the reflux ratio is greater than or equal to 2; and recovering a fatty alcohol product stream comprising the first fatty alcohol species and the second fatty alcohol species from an outlet of the distillation column, wherein the outlet is located above a feed inlet and below an overhead product outlet, wherein the fatty alcohol product stream comprises a first mass percentage of the first fatty alcohol species ($M_1$), and a second mass percentage of the second fatty alcohol species ($M_2$), and wherein a fatty alcohol mass ratio ($M_1/M_2$) of the fatty alcohol product stream is the first mass percentage divided by the second mass percentage, and wherein the fatty alcohol mass ratio is greater than or equal to 2.0.

Embodiment 2

A method of producing fatty alcohols comprises: introducing a fatty alcohol feedstock stream to a distillation column; forming a light outlet stream and a heavy outlet stream; condensing at least a portion of the light outlet stream to form a reflux stream; returning the reflux stream to a reflux inlet of the distillation column at a reflux ratio of greater than or equal to 2; and recovering a fatty alcohol product stream from an outlet of the distillation column, wherein the fatty alcohol product stream comprises a first mass percentage of the first fatty alcohol species ($M_1$), and a second mass percentage of the second fatty alcohol species ($M_2$), and wherein a fatty alcohol mass ratio ($M_1/M_2$) of the fatty alcohol product stream is the first mass percentage divided by the second mass percentage, and wherein the fatty alcohol mass ratio is greater than or equal to 2.0.

Embodiment 3

The method of any of Embodiments 1-2, wherein the first fatty alcohol species comprises a first fatty alcohol comprising 6 carbon atoms and the second fatty alcohol species comprises a second fatty alcohol comprising 8 carbon atoms.

Embodiment 4

The method of any of Embodiments 1-3, wherein the first fatty alcohol species comprises a first fatty alcohol comprising 8 carbon atoms and the second fatty alcohol species comprises a second fatty alcohol comprising 10 carbon atoms

Embodiment 5

The method of any of Embodiments 1-4, wherein the first fatty alcohol species comprises a first fatty alcohol comprising 12 carbon atoms and the second fatty alcohol species comprises a second fatty alcohol comprising 14 carbon atoms.

Embodiment 6

The method of any of Embodiments 1-5, wherein the first fatty alcohol species comprises a first fatty alcohol comprising 16 carbon atoms and the second fatty alcohol species comprises a second fatty alcohol comprising 18 carbon atoms.

Embodiment 7

The method of any of Embodiments 1-6, wherein the reflux ratio is greater than or equal to 10.

Embodiment 8

The method of any of Embodiments 1-7, wherein the reflux ratio is greater than or equal to 25.

Embodiment 9

The method of any of Embodiments 1-8, wherein the reflux ratio is greater than or equal to 45.

Embodiment 10

The method of any of Embodiments 1-9, further comprising achieving a fatty alcohol mass ratio of the fatty alcohol product stream of 2.0 to 3.0 by adjusting the reflux ratio.

Embodiment 11

The method of any of Embodiments 1-10, further comprising achieving a fatty alcohol mass ratio of the fatty alcohol product stream of 2.15 to 2.45.

Embodiment 12

The method of any of Embodiments 1-11, wherein the fatty alcohol product stream comprises a mass percent of the first fatty alcohol of 70-75 mass % and a mass percent of the second fatty alcohol of 25-30 mass %.

Embodiment 13

The method of any of Embodiments 1-12, wherein the reflux ratio is greater than or equal to 10 and the fatty alcohol mass ratio of the fatty alcohol product stream of 2.30 to 2.36.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. A method of producing fatty alcohols comprising:
introducing a fatty alcohol feedstock stream comprising a first fatty alcohol species and a second fatty alcohol species to a distillation column; wherein the first fatty alcohol species comprises fewer carbon atoms than the second fatty alcohol species;
separating the fatty alcohol feedstock stream by a distillation process to form a light outlet stream and a heavy outlet stream;
condensing at least a portion of the light outlet stream to form a reflux stream comprising a reflux mass flow rate and a light product stream comprising a light product mass flow rate;
returning the reflux stream to a reflux inlet of the distillation column at a reflux ratio defined as the reflux mass flow rate divided by the light product mass flow rate, wherein the reflux ratio is greater than or equal to 2; and
recovering a fatty alcohol product stream comprising the first fatty alcohol species and the second fatty alcohol species from an outlet of the distillation column, wherein the outlet is located above a feed inlet and below an overhead product outlet, wherein the fatty alcohol product stream comprises a first mass percentage of the first fatty alcohol species ($M_1$), and a second mass percentage of the second fatty alcohol species ($M_2$), and wherein a fatty alcohol mass ratio ($M_1/M_2$) of the fatty alcohol product stream is the first mass percentage divided by the second mass percentage, and wherein the fatty alcohol mass ratio is greater than or equal to 2.0.

2. A method of producing fatty alcohols comprises:
introducing a fatty alcohol feedstock stream to a distillation column;
forming a light outlet stream and a heavy outlet stream;
condensing at least a portion of the light outlet stream to form a reflux stream;
returning the reflux stream to a reflux inlet of the distillation column at a reflux ratio of greater than or equal to 2; and
recovering a fatty alcohol product stream from an outlet of the distillation column, wherein the fatty alcohol product stream comprises a first mass percentage of the first fatty alcohol species ($M_1$), and a second mass percentage of the second fatty alcohol species ($M_2$), and wherein a fatty alcohol mass ratio ($M_1/M_2$) of the fatty alcohol product stream is the first mass percentage divided by the second mass percentage, and wherein the fatty alcohol mass ratio is greater than or equal to 2.0.

3. The method of claim 1, wherein the first fatty alcohol species comprises a first fatty alcohol comprising 6 carbon atoms and the second fatty alcohol species comprises a second fatty alcohol comprising 8 carbon atoms.

4. The method of claim 1, wherein the first fatty alcohol species comprises a first fatty alcohol comprising 8 carbon atoms and the second fatty alcohol species comprises a second fatty alcohol comprising 10 carbon atoms.

5. The method of claim 1, wherein the first fatty alcohol species comprises a first fatty alcohol comprising 12 carbon atoms and the second fatty alcohol species comprises a second fatty alcohol comprising 14 carbon atoms.

6. The method of claim 1, wherein the first fatty alcohol species comprises a first fatty alcohol comprising 16 carbon atoms and the second fatty alcohol species comprises a second fatty alcohol comprising 18 carbon atoms.

7. The method of claim 1, wherein the reflux ratio is greater than or equal to 10.

8. The method of claim 1, wherein the reflux ratio is greater than or equal to 25.

9. The method of claim 1, wherein the reflux ratio is greater than or equal to 45.

10. The method of claim 1, further comprising achieving a fatty alcohol mass ratio of the fatty alcohol product stream of 2.0 to 3.0 by adjusting the reflux ratio.

11. The method of claim 1, further comprising achieving a fatty alcohol mass ratio of the fatty alcohol product stream of 2.15 to 2.45.

12. The method of claim 1, wherein the fatty alcohol product stream comprises a mass percent of the first fatty alcohol of 70 mass % to 75 mass % and a mass percent of the second fatty alcohol of 25 mass % to 30 mass %.

13. The method of claim 1, wherein the reflux ratio is greater than or equal to 10 and the fatty alcohol mass ratio of the fatty alcohol product stream of 2.30 to 2.36.

14. The method of claim 2, wherein the first fatty alcohol species comprises a first fatty alcohol comprising 6 carbon atoms and the second fatty alcohol species comprises a second fatty alcohol comprising 8 carbon atoms; or wherein the first fatty alcohol species comprises a first fatty alcohol comprising 8 carbon atoms and the second fatty alcohol species comprises a second fatty alcohol comprising 10 carbon atoms;

wherein the first fatty alcohol species comprises a first fatty alcohol comprising 12 carbon atoms and the second fatty alcohol species comprises a second fatty alcohol comprising 14 carbon atoms; or wherein the first fatty alcohol species comprises a first fatty alcohol comprising 16 carbon atoms and the second fatty alcohol species comprises a second fatty alcohol comprising 18 carbon atoms.

15. The method of claim 2, wherein the reflux ratio is greater than or equal to 10.

16. The method of claim 2, wherein the reflux ratio is greater than or equal to 25.

17. The method of claim 2, wherein the reflux ratio is greater than or equal to 45.

18. The method of claim 2, further comprising achieving a fatty alcohol mass ratio of the fatty alcohol product stream of 2.0 to 3.0 by adjusting the reflux ratio.

19. The method of claim 2, further comprising achieving a fatty alcohol mass ratio of the fatty alcohol product stream of 2.15 to 2.45.

20. The method of claim 2, wherein the reflux ratio is greater than or equal to 10 and the fatty alcohol mass ratio of the fatty alcohol product stream of 2.30 to 2.36.

\* \* \* \* \*